US00PP13900P39

(12) United States Plant Patent
Pieters

(10) Patent No.: US PP13,900 P3
(45) Date of Patent: Jun. 24, 2003

(54) CHRYSANTHEMUM PLANT NAMED 'GEDI ONE CEL'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 20 days.

(21) Appl. No.: 09/873,959

(22) Filed: Jun. 4, 2001

(65) Prior Publication Data

US 2002/0188977 P1 Dec. 12, 2002

(51) Int. Cl.[7] ..... A01H 5/00
(52) U.S. Cl. ..... Plt./288
(58) Field of Search ..... Plt./288, 287

(56) References Cited

U.S. PATENT DOCUMENTS

| | | | | |
|---|---|---|---|---|
| PP10,208 P | | 1/1998 | Pieters | Plt./289 |
| PP11,637 P | | 11/2000 | Noodelijk | Plt./288 |
| PP12,259 P2 | * | 12/2001 | Pieters | Plt./294 |

* cited by examiner

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a decorative type inflorescence, consistent flowering response to short days, blooming consistently after 49 days of short day length, free branching habit, white ray florets, very uniform round growth habit, and a large quantity of blooms per flowering branch.

1 Drawing Sheet

LATIN NAME

*Dendranthema morifolium.*

VARIETY

Figure 1:
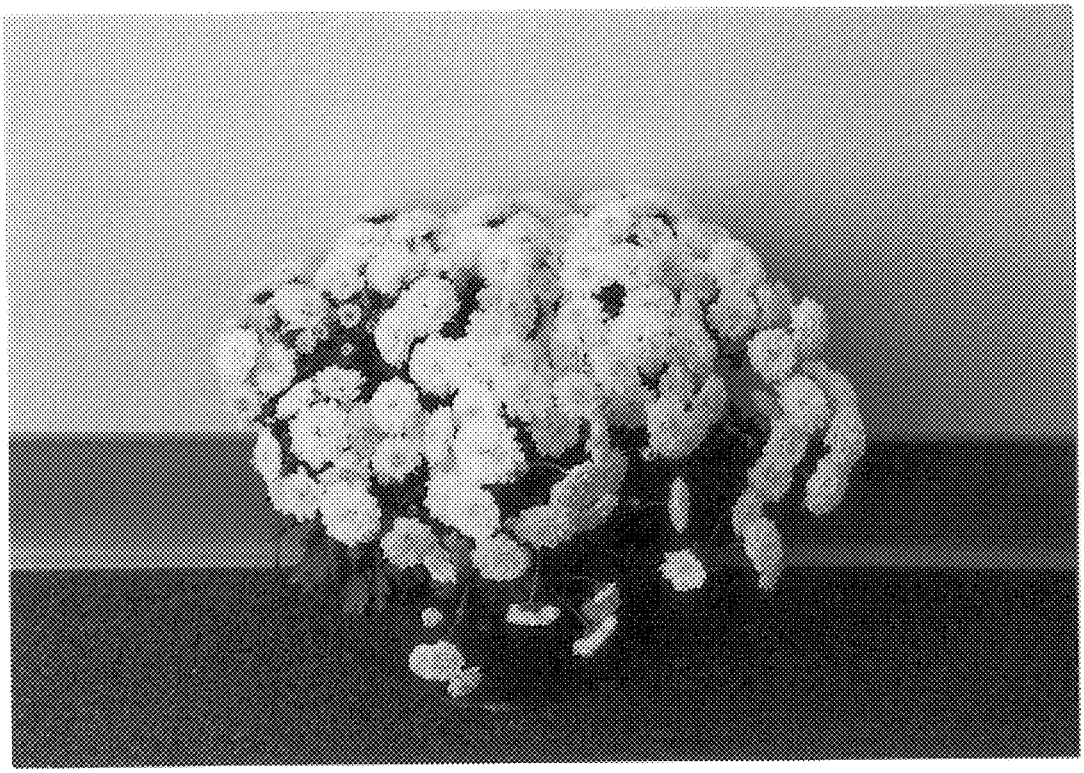

'Gedi One Cel'.

BACKGROUND OF THE INVENTION

The present invention relates to a new and distinct cultivar of Chrysanthemum plant, herein after referred to by the cultivar name 'Gedi One Cel.'

This new cultivar originated from hybridization of a female parent Chrysanthemum cultivar 'Pinos' (U.S. Plant Pat. No. 10,208) with a male parent Chrysanthemum cultivar 'Gedi Wo' (U.S. Plant Pat. No. 12,259). The new cultivar was discovered by the inventor in October 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'Gedi One Cel' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi One Cel.' These characteristics in combination distinguish 'Gedi One Cel' as a new and distinct Chrysanthemum:

1. Decorative type inflorescence;
2. Consistent flowering response to short days, blooming consistently after 49 days of short day length;
3. Free branching habit;

4. White ray florets;
5. Very uniform round growth habit; and
6. Large quantity of blooms per flowering branch.

Plants of the new cultivar are similar to plants of the parent cultivar, 'Pinos,' in most horticultural characteristics, however, when grown under identical environmental conditions, plants of the new cultivar differed from plants of the cultivar 'Pinos' in the following characteristics:

1. The new cultivar has more blooms per flowering branch;
2. The new cultivar has different color ray florets;
3. The new cultivar has a wider diameter bloom; and
4. The new cultivar is taller and wider.

Plants of the new cultivar are similar to plants of the parent cultivar, 'Gedi Wo,' in most horticultural characteristics, however, when grown under identical environmental conditions, plants of the new cultivar differed from plants of the cultivar 'Gedi Wo' in the following characteristics:

1. The new cultivar has a different flower type;
2. The new cultivar is taller and wider; and
3. The new cultivar has a wider diameter bloom.

The new cultivar can be compared to the Chrysanthemum cultivar 'Odysseus' (disclosed in Plant Pat. No. 11,637). However plants of the new Chrysanthemum differed from the plants of the cultivar 'Odysseus' in the following characteristics:

1. The new cultivar naturally blooms 2 weeks later;
2. The new cultivar has a more flexible plant habit;
3. The new cultivar has a more round plant shape and greater branching; and
4. The new cultivar has more blooms per flowering branch.

BRIEF DESCRIPTION OF THE PHOTOGRAPHS

The photograph shows a plant of 'Gedi One Cel' grown in a 6-inch container. A single cutting was used in the container.

DETAILED BOTANICAL DESCRIPTION

In the following description, color references are made to The Royal Horticultural Society Colour Chart except where general terms of ordinary dictionary significance are used. The following observations and measurements describe 70 day old plants grown in a commercial field in Oxnard, Calif. in the month of September 2000. The plants were started from rooted cuttings. The growing conditions range from 60° to 65° F. at night to 70° to 85° F. during the day. Measurements and numerical values represent averages of typical flowering types.

Botanical classification: *Dendranthema morifolium* cultivar 'Gedi One Cel'.
Commercial classification: Garden-type Chrysanthemum.
Parentage: Hybridization of female parent Chrysanthemum cultivar 'Pinos' (U.S. Plant Pat. No. 10,208) with male parent Chrysanthemum cultivar 'Gedi Wo' (U.S. Plant Pat. No. 12,259).

PROPAGATION

Time to rooting: 7 to 14 days at approximately 21° C.
Root description: Fine, fibrous.

PLANT

Growth habit: Mounding herbaceous perennial.
Height: Approximately 20 cm.
Growth rate: Moderate.
Plant spread: Approximately 26 cm.
Branching characteristics: Free Branching.
Length of lateral branches: Approximately 17 cm.
Internode length: Approximately 1.3 cm.
Number of leaves per lateral branch: Approximately 19.

FOLIAGE

Leaf:
- *Arrangement.*—Alternate.
- *Average length.*—Approximately 5.5 cm.
- *Average width.*—Approximately 3.5 cm.
- *Shape of blade.*—Ovate.
- *Apex.*—Acuminate.
- *Base.*—Attenuate.
- *Attachment.*—Stalked.
- *Margin.*—Pinnately lobed and toothed.
- *Texture of top surface.*—Lightly pubescent.
- *Texture of bottom surface.*—Lightly pubescent.
- *Color.*—young foliage upper side: Near 147A young foliage under side: Near 147A mature foliage upper side: Near 147B mature foliage under side: Near 147B venation upper side: Near 147C venation under side: Near 147C.

Petiole:
- *Average length.*—Approximately 1.5 cm.
- *Average diameter.*—Approximately 0.2 cm.
- *Color.*—Near 137C.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the last week in September.
- *Number of inflorescences per stem.*—Approximately 13.
- *Inflorescence diameter.*—Approximately 3.3 cm.
- *Inflorescence depth.*—Approximately 1.0 cm.
- *Inflorescence longevity on plant: Approximately* 26–29 days.
- *Persistence.*—Persistent.
- *Fragrance.*—Not present.

Ray florets:
- *Appearance.*—Matte.
- *Texture.*—Shiny.
- *Average number per flower.*—Approximately 162 .
- *Shape.*—Oblanceolate.
- *Margin.*—Entire.
- *Apex.*—Obtuse.
- *Length.*—Approximately 1.4 cm.
- *Width.*—Approximately 0.6 cm.
- *Color.*—upper surface at first opening: Near 154B upper surface at maturity: Near 155B upper surface at fading: Near 155A under surface at first opening: Near 154A under surface at maturity: Near 155B under surface at fading: Near 154A.

Disc florets:
- *Appearance.*—Shiny.
- *Texture.*—Smooth.
- *Average number per flower.*—Approximately 15.
- *Shape.*—Cylindric.
- *Apex.*—Obtuse.
- *Average length.*—Approximately 0.3 cm.
- *Average width.*—Approximately 0.1 cm.
- *Color.*—at first opening: Near 154B at maturity: Near 154C at fading: Near 154C.

Peduncle:
- *Length.*—at terminal end (shortest): Approximately 3.5 cm at lateral end (longest): Approximately 6 cm.
- *Diameter.*—Approximately 0.3 cm.
- *Strength.*—Moderate.
- *Color.*—Near 147B.
- *Habit.*—Erect.
- *Surface texture.*—Lightly pubescent.

Inflorescence bud:
- *Length.*—Approximately 0.6 cm.
- *Diameter.*—Approximately 0.6 cm.
- *Form.*—Globular.
- *Color.*—Near 154C.

Phyllaries:
- *Appearance.*—Matte.
- *Texture.*—Lightly pubescent.
- *Number.*—Approximately 20.
- *Shape.*—Ovate.
- *Margin.*—Entire.
- *Apex.*—Acute.
- *Diameter.*—0.2 cm.
- *Length.*—0.3 cm.
- *Color.*—upper side: Near 137C under side: Near 137B.

REPRODUCTIVE ORGANS

Ray florets:

*Number of pistils per flower:* 1.

*Stigma shape*—2 branched.

*Stigma color*—Near 12A.

*Stigma length.*—Approximately 0.1 cm.

*Style color.*—Near 154C.

*Style length*—Approximately 0.2 cm.

*Stamens.*—Absent.

Disc florets:

*Number of pistils per flower.*—1.

*Stigma shape.*—Cylindric.

*Style length.*—Approximately 0.5 cm.

*Number of stamens per flower.*—Approximately 5.

*Anther shape.*—Tubular.

*Anther color.*—Near 12A.

*Pollen color.*—Near 12A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests have been observed in this cultivar.

What is claimed is:

1. A new and distinct variety of Chrysanthemum plant named 'Gedi One Cel' as herein illustrated and described.

* * * * *